(12) United States Patent
Adda

(10) Patent No.: US 9,523,606 B2
(45) Date of Patent: Dec. 20, 2016

(54) METHOD AND APPARATUS FOR TESTING MATERIALS

(71) Applicant: Airbus Operations Limited, Bristol (GB)

(72) Inventor: Laid Adda, Bristol (GB)

(73) Assignee: Airbus Operations Limited, Bristol (GB)

( * ) Notice: Subject to any disclaimer, the term of this patent is extended or adjusted under 35 U.S.C. 154(b) by 0 days.

(21) Appl. No.: 14/807,273

(22) Filed: Jul. 23, 2015

(65) Prior Publication Data

US 2016/0025566 A1 Jan. 28, 2016

(30) Foreign Application Priority Data

Jul. 23, 2014 (GB) .................................. 1413083.5

(51) Int. Cl.
| | |
|---|---|
| *G01J 3/02* | (2006.01) |
| *G01N 21/35* | (2014.01) |
| *G01N 21/27* | (2006.01) |
| *G01N 21/3563* | (2014.01) |
| *G01J 3/28* | (2006.01) |
| *G01N 21/84* | (2006.01) |

(52) U.S. Cl.
CPC ............. *G01J 3/0297* (2013.01); *G01J 3/28* (2013.01); *G01N 21/274* (2013.01); *G01N 21/3563* (2013.01); *G01N 2021/3595* (2013.01); *G01N 2021/8472* (2013.01); *G01N 2201/0221* (2013.01)

(58) Field of Classification Search
CPC ... G01J 3/0297; G01J 3/28; G01N 2021/3595; G01N 2021/8472; G01N 21/274; G01N 21/3563; G01N 2201/0221
See application file for complete search history.

(56) References Cited

U.S. PATENT DOCUMENTS

| | | |
|---|---|---|
| 5,457,319 A | 10/1995 | Moe et al. |
| 5,473,161 A | 12/1995 | Nix et al. |
| 8,319,182 B1 | 11/2012 | Brady et al. |

(Continued)

FOREIGN PATENT DOCUMENTS

| | | |
|---|---|---|
| EP | 1 070 956 | 1/2001 |
| EP | 2 138 829 | 12/2009 |

(Continued)

OTHER PUBLICATIONS

Wolfrum J et al., "Rapid Evaluation of long-term thermal degradation of carbon fibre epoxy composites.", Composites Science and Technology, Elsevier, UK, vol. 69, No. 3-4, Mar. 2009, pp. 523-530.*

(Continued)

*Primary Examiner* — Mark R Gaworecki
(74) *Attorney, Agent, or Firm* — Nixon & Vanderhye P.C.

(57) ABSTRACT

A method and apparatus for testing materials for testing materials using infrared spectrometry. Calibration of an infrared spectrometer for use in testing materials including the steps of: selecting variables which have the potential to influence the physical characteristics of a composite used in the aerospace industry, selecting values for each variable and inputting the variable and values into a design of experiments model, thereby obtaining a sample test matrix.

6 Claims, 4 Drawing Sheets

(56) References Cited

U.S. PATENT DOCUMENTS

| | | | |
|---|---|---|---|
| 2002/0027649 | A1 | 3/2002 | Chudner |
| 2003/0109998 | A1 | 6/2003 | Lorenz et al. |
| 2003/0111606 | A1 | 6/2003 | Berghmans et al. |
| 2009/0213361 | A1 | 8/2009 | Vander Rhodes et al. |
| 2009/0257046 | A1 | 10/2009 | Dean et al. |
| 2009/0321648 | A1 | 12/2009 | Shelley et al. |
| 2009/0323757 | A1* | 12/2009 | Werner .............. G01N 25/72 374/45 |
| 2010/0168590 | A1 | 7/2010 | Kasama |
| 2010/0276578 | A1 | 11/2010 | Shelley et al. |
| 2011/0001047 | A1 | 1/2011 | Shelley et al. |
| 2011/0085030 | A1 | 4/2011 | Poe et al. |
| 2011/0168897 | A1 | 7/2011 | Buffington et al. |
| 2013/0261876 | A1 | 10/2013 | Froom et al. |

FOREIGN PATENT DOCUMENTS

| | | |
|---|---|---|
| EP | 2 343 531 | 7/2011 |
| EP | 2 426 480 | 3/2012 |
| EP | 2743677 | 6/2014 |
| JP | 2010197099 | 9/2010 |
| WO | 92/22804 | 12/1992 |
| WO | 9606344 | 2/1996 |
| WO | 02054156 | 7/2002 |
| WO | 2004042375 | 5/2004 |
| WO | 2012040695 | 3/2012 |

OTHER PUBLICATIONS

Dara, I.H. et al., "Heat-damage assessment of carbon-fiber-reinforced polymer composites by diffuse reflectance infrared specroscopy", Journal of Applied Polymer Science, vol. 96, No. 4, Mar. 10, 2005, pp. 1222-1230.*

"Agilent Handheld FTIR Analyzers True Non Destructive Testing of Advanced Materials", www.agilent.com/chem/nondestructivetesting, published May 3, 2013, two pages.

Search Reported cited in GB 1413080.1, completed Jan. 19, 2015, five pages.

European Search Report cited in EP 15 17 6714, completed Dec. 15, 2015, two pages.

Roger Jones et al., "Monitoring Ambient-Temperature Aging of a Carbon-Fiber/Epoxy Composite Prepreg With Photoacoustic Spectroscopy", Composites: Part A 39 (2008), pp. 965-971.

Search Report cited in GB 1413083.5, mailed Jan. 20, 2015, one page.

EP Search Report cited in EP 15 17 6715, mailed Dec. 15, 2015, three pages.

Harald Martens et al. "Multivariate Calibration", 1989, Wiley, Chapter 6,18 pages.

J. Wolfrum et al., "Rapid Evaluation of Long-Term Thermal Degradation of Carbon Fibre Epoxy Composites", Composites Science and Technology 69 (2009), pp. 523-530.

I- H. Dara et al., "Heat-Damage Assessment of Carbon-Fiber-Reinforced Polymer Composites by Diffuse Reflectance Infrared Spectroscopy", 2004, 9 pages.

Tucker Howie et al., "The Detection of Incipient Thermal Damage of CFRP Using FTIR", 2014, 12 pages.

R. Kunic et al., "Life Expectancy Prediction and Application Properties of Novel Polyurethane Based Thickness Sensitive and Thickness Insensitive Spectrally Selective Paint Coatings for Solar Absorbers", Solar Energy Materials & Solar Cells 95, (2011) 2965-2975.

Govindarajan Naganathan et al., "Visible/Near-Infrared Hyperspectral Imaging for Beef Tenderness Prediction", Computers and Electronics in Agriculture 64 (2008) 225-233.

C. Petisco et al., "Near-Infrared Reflectance Spectroscopy as a Fast and Non-Destructive Tool to Predict Foliar Organic Constituents of Several Woody Species", Anal Bioanal Chem (2006) 386:1823-1833.

* cited by examiner

| Config. N° | Lay-up | ECF | Paint | Heating ramp | Cooling ramp | Temperature to reach | Dwell (time) at equilibrium | Wet ageing @70C |
|---|---|---|---|---|---|---|---|---|
| Config.1 | 25/50/25 | Yes | No | High | Low | 240 | Yes | No |
| Config.2 | 50/40/10 | No | Yes | Low | Low | 240 | No | No |
| Config.3 | 25/50/25 | No | Yes | High | Low | 200 | Yes | No |
| Config.4 | 25/50/25 | No | No | High | Medium | 200 | No | No |
| Config.5 | 50/40/10 | No | Yes | High | Medium | 200 | No | Yes |
| Config.6 | 50/40/10 | Yes | Yes | Low | Low | 200 | Yes | Yes |
| Config.7 | 25/50/25 | No | No | Low | Low | 220 | No | Yes |
| Config.8 | 25/50/25 | No | Yes | Low | Medium | 240 | Yes | Yes |
| Config.9 | 50/40/10 | No | No | Low | Medium | 220 | Yes | No |
| Config.10 | 25/50/25 | Yes | Yes | Low | Medium | 240 | No | No |
| Config.11 | 50/40/10 | Yes | No | Low | Low | 200 | No | No |
| Config.12 | 50/40/10 | Yes | No | High | Medium | 240 | No | Yes |
| Config.13 | 25/50/25 | Yes | Yes | High | Low | 220 | No | No |
| Config.14 | 50/40/10 | Yes | Yes | High | Medium | 220 | Yes | No |
| Config.15 | 25/50/25 | Yes | No | Low | Medium | 200 | Yes | Yes |

Fig. 5

METHOD AND APPARATUS FOR TESTING MATERIALS

RELATED APPLICATION

This application claims priority to United Kingdom (GB) application no. GB 1413083.5 filed Jul. 23, 2014, the entirety of which is incorporated by reference.

BACKGROUND OF THE INVENTION

The present disclosure relates to a method and apparatus for testing materials. More particularly, but not exclusively, this invention concerns a method and apparatus for testing materials using infrared spectrometry. The invention also concerns the calibration of an infrared spectrometer for use in testing materials using infrared spectrometry.

Infrared spectrometry may be used to measure and/or monitor physical properties of composite materials, such as advanced polymer matrix composites with high strength fibers. Composite materials are used extensively in the aerospace industry. The aerospace industry has exacting standards relating to materials quality. During the lifetime of an aircraft, various events may occur which can damage part of the aircraft. Example of events include lightning strikes, holes being drilled in the aircraft during manufacturing or maintenance procedures, electrical arching, and laser treatment of materials during manufacturing or maintenance procedures. These events may result in the thermal degradation of composite materials making up the aircraft. Alternatively, during the manufacture or maintenance of an aircraft or aircraft component, a composite material may be overheated, for example during the curing of a composite material.

European patent publication number EP 2138829 discloses measuring the thermal effect of composite materials used in the aerospace industry using mid-range infrared spectroscopy. A hand-held infrared spectrometer is used to take measurements of a material, with the infrared spectra compared to a database of spectra to determine a physical property of that material. The hand-held infrared spectrometer is calibrated using a multivariate calibration process. Such a process can be time consuming.

SUMMARY OF THE INVENTION

The present invention seeks to mitigate the above-mentioned problems. Alternatively or additionally, the present invention seeks to provide an improved method of calibrating an infrared spectrometer.

The present invention provides, according to a first embodiment, a method of calibrating an infrared spectrometer for testing composites in the aerospace industry, comprising the steps of:
  a) selecting a plurality of variables which have the potential to influence the physical characteristics of a composite used in the aerospace industry;
  b) selecting a plurality of values for each variable;
  c) inputting the variables and values into a design of experiments model;
  d) thereby obtaining a sample test matrix.

The invention may comprise a method of calibrating an infrared spectrometer for testing composites in the aerospace industry for thermal effects. Thermal effects may occur as a result of lightning strikes, holes being drilled in an aircraft during manufacturing or maintenance procedures, electrical arching, and laser treatment of materials during manufacturing or maintenance procedures. These events may result in the thermal degradation of composite materials making up an aircraft or aircraft component. Alternatively, during the manufacture or maintenance of an aircraft or aircraft component, a composite material may be overheated, for example during the curing of a composite material.

Using the design of experiments method may reduce the testing required to obtain a results database for an infrared spectrometer to analyse results in comparison to. Accuracy of calibration may be increased, especially advantageous for safety and highly regulated products. The risk of not being able to characterise damage to a sample may be reduced. More than one resin type may be calibrated during the same calibration process. Multiple properties of the material may be tested without requiring a significant increase in testing costs. The method may provide a more accurate history of the damage done to a sample.

The plurality of variables may include the configuration of the composite lay-up. For example, the lay-up may comprise a 50/40/10 directed lay up or a 25/50/25 quasi-isotropic lay-up. The plurality of variables may include whether or not the composite comprises an expanded copper foil (ECF). The plurality of variables may include whether or not the composite has been painted. The plurality of variables may include whether or not the composite has been wet aged.

The plurality of variables may include the heating ramp in a composite curing process. The heating ramp may comprise a sample being thrown in a hot oven (high heating ramp) or a sample being heated at two (2) degrees Celsius per minute (low heating ramp). The plurality of variables may include the maximum temperature reached by a sample. For example, the maximum temperature reached may be 200, 220, or 240 degrees Celsius. The plurality of variables may include whether or not the sample is allowed any dwell time. For example. The sample may be allowed dwell time of three hours, or no dwell time (less than one hour). The plurality of variables may include the cooling ramp of the sample, meaning how quickly the sample is cooled. The sample may be cooled at 7 degrees Celsius per minute (medium cooling ramp) or 2 degrees Celsius per minute (low cooling ramp).

The method of calibration may comprise testing a plurality of composite samples according to the test matrix. The method may comprise the step of collating the infrared spectra detected by the infrared spectrometer with measured physical characteristics of a sample. The measured physical characteristics may include the bearing strength of a sample, the plain compression strength of a sample, and/or the interlaminar shear strength of a sample. The correlation of infrared spectra and measured physical characteristics may form a database of measurement results. The database of measurement results may be interrogated by the infrared spectrometer when taking a measurement of an aircraft or aircraft component, in order to provide a measurement of the physical characteristics of the aircraft or aircraft component.

According to a second embodiment of the invention, there is provided a method of testing an aircraft or aircraft component comprising composite material, the method comprising the steps of:
  a) taking a measurement of the composite material using an infrared spectrometer, thereby obtaining an infrared spectrum,
  b) comparing the infrared spectrum to a database of infrared spectra and correlated physical characteristics acquired according to the first aspect of the invention;

c) thereby providing a value relating to a physical characteristic of the composite material.

According to a third embodiment of the invention, there is provided an infrared spectrometer for testing material characteristics of an aircraft or aircraft component, the infrared spectrometer calibrated as described in relation to the first aspect of the invention.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which:

FIG. 5 shows a test matrix which may be produced by the design of experiments model according to a fifth embodiment of the invention.

DETAILED DESCRIPTION

The invention provides a method of calibrating an infrared spectrometer for taking infrared measurements of composite materials used in the aerospace industry. An example spectrometer which may be used is a handheld infrared spectrometer, such at the 4100 ExoScan Series FTIR™, available from Agilent Technologies, Santa Clara, USA. Using a handheld infrared spectrometer allows an engineer to make an easy assessment of a material onsite. The spectrometer may provide a clear indication of whether a composite material is suitable for use, should be repaired, or replaced, depending on how the material is being used, or would be used. The spectrometer may allow a composite material to be tested after exposure to potential thermal damage.

Figure 1:
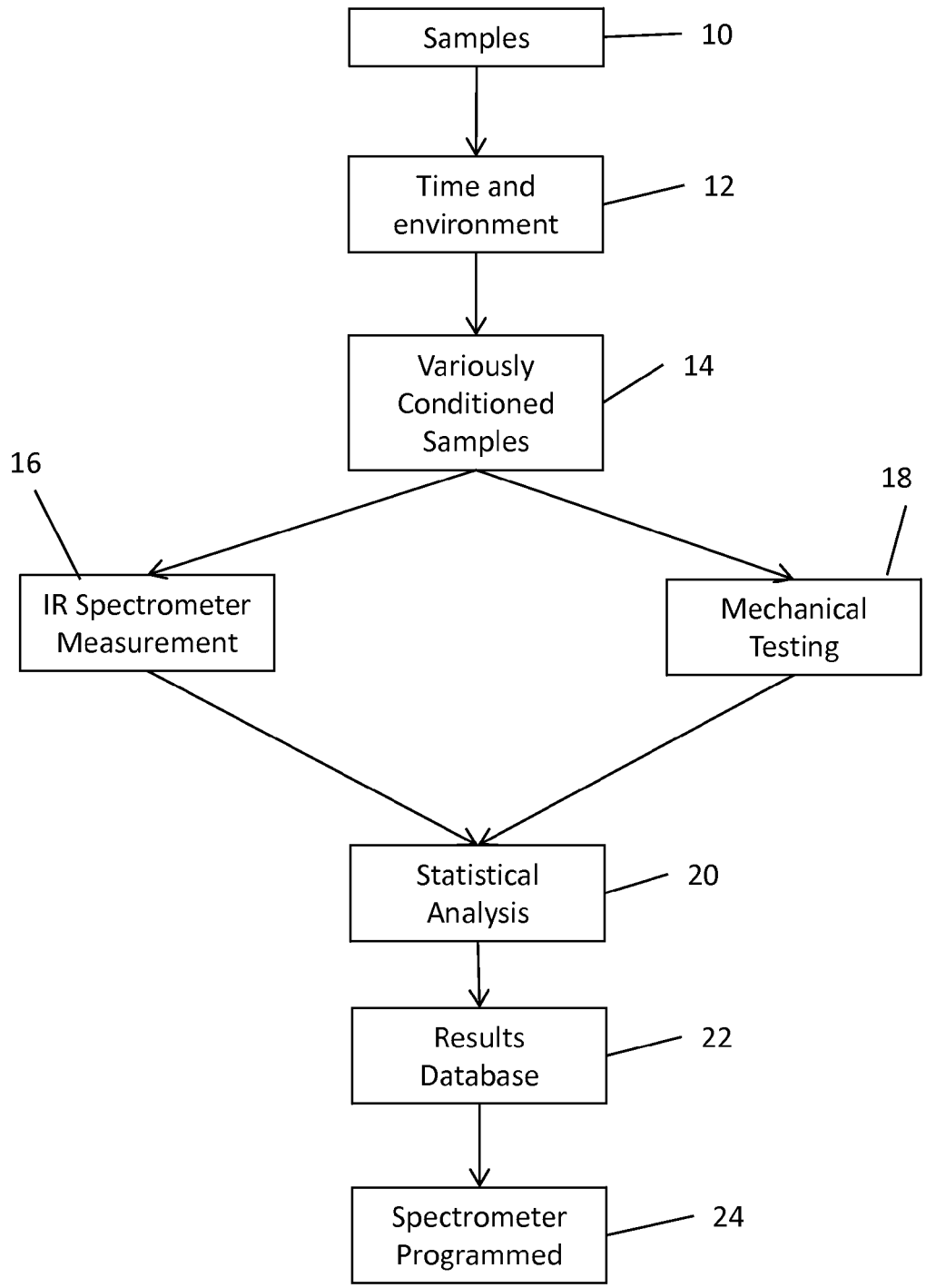
FIG. 1 shows a flow chart relating to a method according to a first embodiment of the invention.

FIG. 1 shows the calibration process according to a first aspect of the invention. Firstly, a number of composite samples are prepared at step 10. These composite samples are stored for a set time under set environmental conditions, as indicated by step 12. The samples are stored for a spread of different times and under different environmental conditions in order to provide a wide sample base for the calibration process. The range of conditions and number of samples required to give appropriate accuracy to the method is expanded upon with reference to FIG. 4. This results in a collection of variously conditioned composite samples 14. Each of these samples is then examined by an infrared spectrometer 16, and also mechanically tested 18. Therefore, for each sample, an infrared spectrum is obtained, together with an assessment of one or more mechanical properties of the sample. These measurement results are stored in a database, and statistical analysis is performed to correlate infrared spectra with the physical properties of the sample, as shown in step 20. The analysis of the samples includes classifying samples as either "acceptable" or "not acceptable" as indicated by step 22. In this case, "not acceptable" indicates a material is no longer suitable for use and should be repaired or replaced, and "acceptable" indicates that a material is suitable for use and does not require repair or replacement. The output may be in the form of different lights being illuminated on the testing device, or a screen associated with the testing device indicating the results, either as words and/or colours.

In an alternative embodiment, the output may comprise a measure of the mechanical property of the sample, for example tensile strength, such that future infrared measurements of similar samples results in the display of the same mechanical reading. A skilled user may assess the value attributed to the measured mechanical property in order to decide whether or not the measured material requires any repair or replacement.

Figure 2:
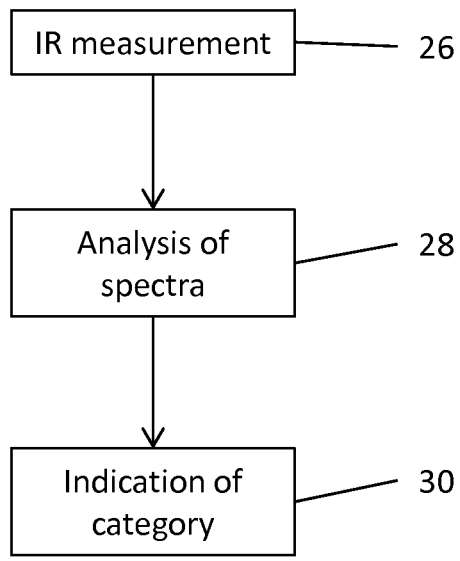
FIG. 2 shows a flow chart relating to a method according to a second embodiment of the invention.

As the final step 24 in the calibration process, the infrared spectrometer is programmed with the results data such that future analysis of measurement data may be performed automatically, as described further with respect to FIG. 2.

FIG. 2 shows a method according to a second embodiment of the invention. An infrared spectrometer, calibrated as described with reference to FIG. 1, is used to take a measurement of a sample of composite material, as shown at step 26. The measurement spectra is then analysed by the spectrometer at step 28, where a comparison is made to the stored spectra results. The analysis of the spectra results in the determination of which category, acceptable or not acceptable, the composite material falls into, and the spectrometer outputs a user readable indication of the category at step 30. Once an infrared spectrometer has been calibrated correctly, infrared spectrometers with the same specifications, for example the same make and model of infrared spectrometer, may be programmed with the appropriate calibration data without requiring the actual calibration process to be repeated. In an alternative embodiment, the indication of category 30 may be replaced by an indication of a value relating to a mechanical property of the measured material, such as tensile strength.

Figure 3:
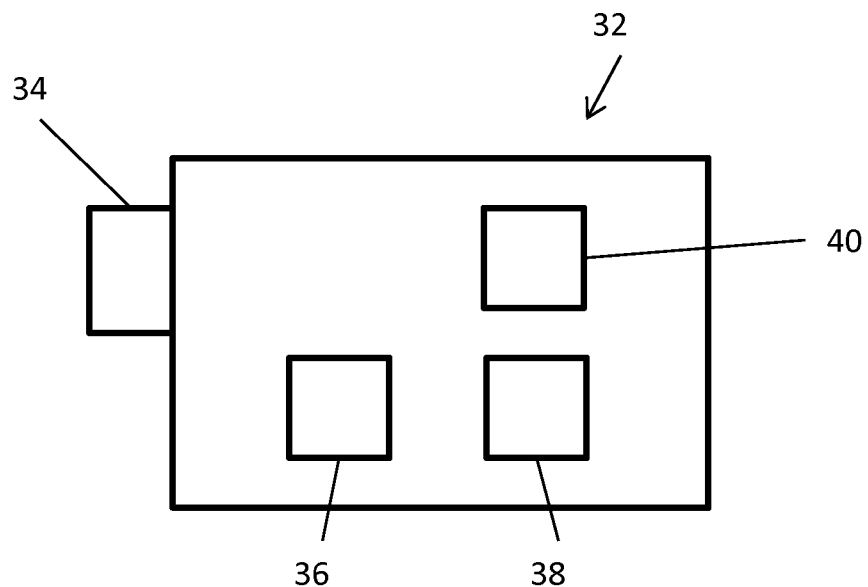
FIG. 3 shows a schematic representation of an infrared spectrometer according to a third embodiment of the invention.

FIG. 3 shows a spectrometer according to a third aspect of the invention. The spectrometer 32 is a handheld spectrometer comprising an infrared measurement device 34, a control unit 36, and a memory unit 38, and a display 40. The infrared measurement device is of common construction as would be understood by a skilled person. An example infrared measurement device is the hand-held IR spectrometer, 4100 ExoScan Series FTIR, available from Agilent Technologies, Santa Clara, USA. The memory unit 38 includes a database of correlations between infrared spectra and the measurement results obtained during the calibration process as described with reference to FIG. 1. In order to take a measurement, a user holds the infrared measurement device up to a material and activates the device. The measurement results are analysed by the control unit 36 and compared to the database of results. Depending on the results of the analysis, the display 40 indicates what category the material falls into.

Figure 4:
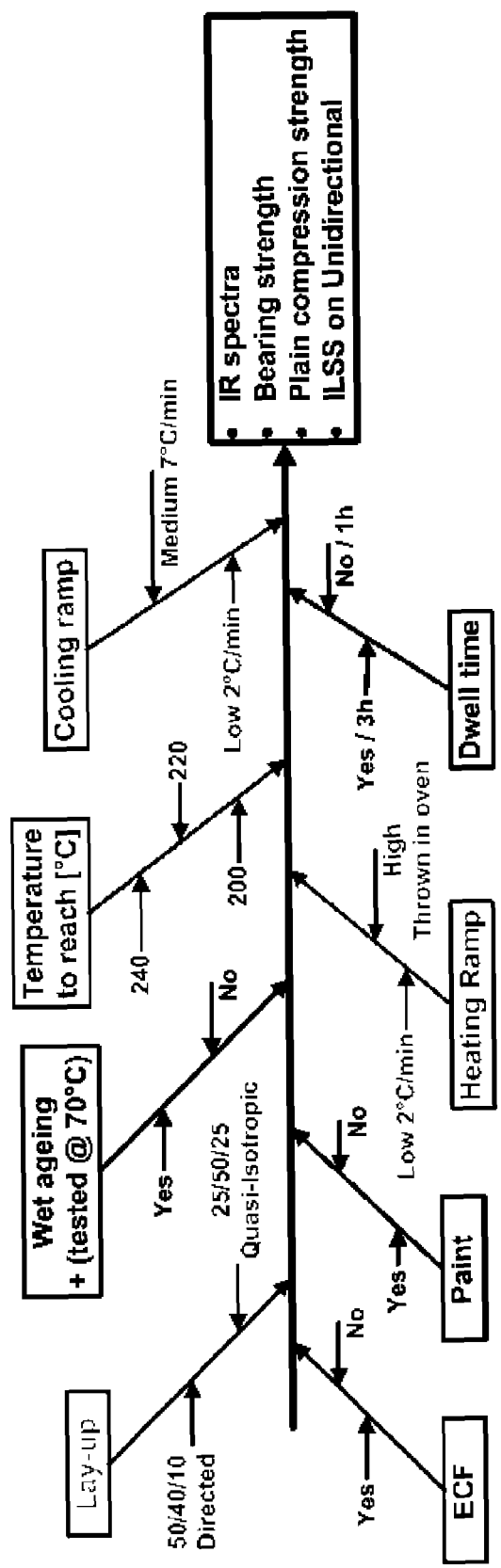
FIG. 4 shows a plurality of variables which may be input into a design of experiments model according to a fourth embodiment of the invention.

FIG. 4 shows a number of variables that may be input into a design of experiments model for determining how the samples are conditioned for the calibration process as described above. The variables include:

Lay-up—for example the sample lay-up may be 50/40/10 directed, or 25/50/25 quasi-isotropic;

Expanded Copper Foil (ECF)—whether the sample includes or does not include expanded copper foil;

Paint—whether the sample has been or has not been painted;

Wet aging—whether or not the sample has been wet aged;

Heating ramp—how quickly the sample is heated, for example being thrown in an oven (high) or 2 degrees Celsius per minute (low);

Temperature to reach—the maximum temperature reached, for example 200, 220, or 240 degrees Celsius;

Dwell time—whether the sample is allowed dwell time (3 hours) or no dwell time (1 hour);

Cooling ramp—how quickly the sample is cooled, for example, 7 degrees Celsius per minute (medium) or 2 degrees Celsius per minute (low).

The parameters tested may include the infrared spectra of the sample, the bearing strength of the sample, the plain compression strength of a sample, and the interlaminar shear strength of the sample.

The choice of parameters is dependent on the skilled persons knowledge of composite materials. The parameters are entered into a design of experiments methodology in order to obtain a test matrix necessary to obtain a reliable set of calibration measurements. The test matrix is shown in FIG. 5. As can be seen, 15 configurations are determined sufficient to provide a suitable set of calibration measurements. The skilled person could use a number of computer software packages to run the design of experiments model, including JMP as available from SAS (www.jmp.com—as available July 2014) and the open-source software, R-Project (www.r-project.org—as available July 2014).

This contrasts to testing each possible combination of variables, which with eight variables chosen and two levels per variable (ignoring for simplicity the temperature to reach variable having three levels) would result in 256 configurations being tested. This presents a significant saving in time and cost of calibrating the infrared spectrometer. Each configuration may include three samples being conditioned in the same way, to allow for each of the three mechanical tests to be carried out. The total number of samples required is then 45. This contrasts to testing each configuration with a number of samples, which will end up with a total number of samples in the hundreds or thousands.

An example configuration highlighted in FIG. 5 is configuration 4. In this configuration, the sample has a 25/50/25 lay-up, no ECF, is not painted, experiences a high heating ramp, medium cooling ramp, reaches a maximum temperature of 200 degrees Celsius, does not have any dwell time and is not wet aged.

The test matrix determines the how the samples are conditioned prior to the measurements being taken as described with reference to FIG. 1. In order to provide a reference spectrum, the infrared spectrometer may perform a measurement on a sample prior to the sample being conditioned. For painted samples, a reference spectrum may also be obtained before the raw material is painted, and also after painting but before conditioning to obtain a spectrum associated with the paint. After conditioning, a measurement may be performed on the painted sample to obtain a spectrum associated with the overheated paint, and after the sample has been sanded to remove the paint, to obtain the overheated sample spectrum without the influence of the paint residue.

In order to provide a representative measurement of each of the samples of material, each sample may be notionally sub-divided into a number of "cells". The spectrometer may take a measurement of the spectra of each cell, and obtain an average reading across the whole sample.

Whilst the present invention has been described and illustrated with reference to particular embodiments, it will be appreciated by those of ordinary skill in the art that the invention lends itself to many different variations not specifically illustrated herein. Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise.

The invention is:

1. A method of testing an aircraft or aircraft component comprising composite material, the method comprising:
    calibrating an infrared spectrometer by selecting a plurality of variables which have the potential to influence the physical characteristics of a composite used in the aerospace industry, the calibration further comprises:
        selecting a plurality of values for each variable;
        inputting the variables and values into a design of experiments model, thereby obtaining a sample test matrix;
        testing a plurality of composite samples according to the test matrix, thereby obtaining a number of infrared spectra;
        testing a physical characteristic of the composite samples;
        collating the infrared spectra detected by the infrared spectrometer with the measured physical characteristic of a sample, and
        correlating of infrared spectra and measured physical characteristics to form a database of measurement results, wherein the database of measurement results represents a calibration of the infrared spectrometer;
    the method further comprising:
    taking a measurement of the aircraft or aircraft component comprising composite material using the infrared spectrometer, thereby obtaining an infrared spectrum,
    comparing the infrared spectrum to the database of infrared spectra and correlated physical characteristics; and
    based on the comparison, providing a value relating to a measurement of a physical characteristic of the composite material.

2. The method as claimed in claim 1, wherein the calibration of the infrared spectrometer is for testing composite materials in the aerospace industry for thermal effects.

3. The method as claimed in claim 1, wherein the plurality of variables includes at least one of:

a configuration of the composite lay up;
whether or not the composite material comprises an expanded copper foil (ECF);
whether or not the composite material has been painted;
whether or not the composite material has been wet aged;
a heating ramp in a composite material curing process;
a maximum temperature reached in a composite material curing process;
whether or not the composite material is allowed any dwell time; or
a cooling ramp of the composite material.

4. The method as claimed in claim 1 wherein the measured physical characteristics include at least one of:
a bearing strength of a sample;
a plain compression strength of a sample, or
an interlaminar shear strength of a sample.

5. An infrared spectrometer for testing material characteristics of an aircraft or aircraft component configured to perform the method of claim 1.

6. A method of calibrating an infrared spectrometer comprising:
selecting variables each of which influence one or more physical characteristics of a composite material configured to be a component of an aircraft;
selecting values for each of the variables;
inputting the variables and values into a design of experiments model, thereby obtaining a sample test matrix;
testing samples of the composite material according to the test matrix, wherein the testing generates data of infrared spectra of each of the samples;
testing a physical characteristic of the composite samples;
collating the data of the infrared spectra with the measured physical characteristic of each samples, and
correlating infrared spectra data and measured physical characteristics to create a database of measurement results, wherein the database of measurement results provides a calibration of the infrared spectrometer.

* * * * *